(12) United States Patent
Höfer et al.

(10) Patent No.: US 7,586,305 B2
(45) Date of Patent: Sep. 8, 2009

(54) METHOD FOR DETERMINING THE ABSOLUTE NUMBER OF ELECTRON SPINS IN A SAMPLE OF EXTENDED SIZE

(75) Inventors: Peter Höfer, Ettlingen (DE); Patrick Carl, Walzbachtal (DE)

(73) Assignee: Bruker Biospin GmbH, Rheinstetten (DE)

( * ) Notice: Subject to any disclaimer, the term of this patent is extended or adjusted under 35 U.S.C. 154(b) by 0 days.

(21) Appl. No.: 12/232,395

(22) Filed: Sep. 17, 2008

(65) Prior Publication Data

US 2009/0079429 A1 Mar. 26, 2009

(30) Foreign Application Priority Data

Sep. 20, 2007 (DE) .................. 10 2007 044 939

(51) Int. Cl.
*G01V 3/00* (2006.01)
(52) U.S. Cl. ....................... 324/300; 324/308
(58) Field of Classification Search ............ 324/300, 324/308, 312
See application file for complete search history.

(56) References Cited

U.S. PATENT DOCUMENTS

| | | | |
|---|---|---|---|
| 3,663,952 A * | 5/1972 | Bozanic et al. | 324/315 |
| 6,674,283 B2 * | 1/2004 | Gerald et al. | 324/318 |
| 7,292,035 B2 * | 11/2007 | Habara et al. | 324/316 |
| 2008/0034287 A1 * | 2/2008 | Mills | 715/273 |

FOREIGN PATENT DOCUMENTS

DE 198 39 497 3/2000

* cited by examiner

*Primary Examiner*—Louis M Arana
(74) *Attorney, Agent, or Firm*—Paul Vincent

(57) ABSTRACT

In a method for determining an absolute number of electron spins in an extended sample (3) with the assistance of an apparatus for measuring magnetic resonance, the extended sample (3) is disposed within a measurement volume (2) of a radiofrequency RF resonator (1) of the apparatus during an electron spin resonance measurement (ESR). The method has the following steps: determining a spatial sensitivity profile f of the RF resonator (1) over the measurement volume (2); determining a resonator sensitivity constant c by means of a comparison to the measurement volume (2) of small calibration sample having a known number of electron spins at a particular position within the measurement volume (2); measuring a magnetic resonance signal RS of the extended sample (3) in the apparatus with a known spatial distribution of extended sample (3) within the measurement volume (2); weighting the magnetic resonance signal RS with the integral of the spatial sensitivity profile f of the RF resonator over the partial volume of the measurement volume (2) occupied by the extended sample (3); and determining the number of electron spins $N_S$ in extended sample (3) as a quotient between the weighted resonance signal and the resonator sensitivity constant c. The method facilitates a simpler determination of the absolute number of electron spins in the sample.

8 Claims, 4 Drawing Sheets

METHOD FOR DETERMINING THE ABSOLUTE NUMBER OF ELECTRON SPINS IN A SAMPLE OF EXTENDED SIZE

This application claims Paris Convention priority of DE 10 2007 044 939.0 filed Sep. 20, 2007 the complete disclosure of which is hereby incorporated by reference.

BACKGROUND OF THE INVENTION

The invention concerns a method for the determination of the absolute number of electron spins in a sample of extended size with the assistance of an apparatus for the measurement of magnetic resonance, wherein the extended sample is disposed within a measuring volume of a radio frequency (RF) resonator in an electron spin resonance (ESR) apparatus.

A method of this kind is known e.g. from J. A. Weil et. al., Electron Paramagnetic Resonance, John Wiley and Sons, New York, 1994.

The present invention concerns the measurement of samples using electron spin resonance (ESR). ESR spectroscopy is a method of analytic instrumentation for the investigation of a sample. The sample must thereby have unpaired electrons. Microwave (generally with constant frequency), are irradiated into the sample which is located in a strong magnetic field $B_0$ (the magnetic field $B_0$ is generally modulated).

The chemical composition of the sample can be determined by the absorption properties thereof. The position of the absorption lines can reliably indicate the type of chemical bindings or the associated substances. It is however, often useful to determine the fraction of a particular substance within the sample. In order to do so using ESR spectroscopy, it is necessary to measure the number of electron spins in the sample.

In accordance with J. Weil loc. cit., an absolute quantification can be determined as follows. In addition to the (unknown) sample being measured, a reference sample is prepared which has a known absolute number of electron spins (for example a certain weight amount of a paramagnetic salt) which is otherwise equivalent to the unknown sample, in particular with respect to the type and the sample container as well as with respect to the filling level within the sample container. The required equivalence of the samples with respect to ESR specific properties, include e.g. a so-called saturation behavior and the spectral region in which the ESR lines occur. The unknown sample and the reference sample are thereby measured under the same conditions using ESR. In order to establish equivalent ESR measuring conditions, a so-called double resonator is utilized which has two separate measuring chambers in which the two samples can be inserted. The measurement of the two samples thereby occurs without direct sequential exchange of the sample. This ensures that both samples are measured with the same Q-factor. A double resonator of this kind is e.g. known from Bruker BioSpin GmbH, Rheinstetten, DE, and entitled "ER4105DR EPR resonator". The absolute number of spins in the unknown sample can be derived from the ratio of the respectively obtained ESR amplitudes.

This method has the disadvantage that it is necessary to prepare and measure a similar type of reference sample for each unknown sample. Moreover, the double resonator is difficult and expensive from a constructional point of view. In addition, the same kind of reference samples can only be prepared for liquid samples. However, ESR samples occur in all kinds of states: in powder form as well as in single crystal form.

J. A. Weil also discloses a procedure for relative quantification of electron spins with which ratios between the number of electron spins of a series of similar samples can be determined. Towards this end, a marker probe sample is measured simultaneously with each sample of the series (e.g. the sample of the series and the marker sample are disposed and measured simultaneously in the same resonator. The marker sample produces its own signal (marker) in the absorption spectrum, which must be easily distinguished from the actual signal of the sample of the series (sample signal). The underlying problem with this procedure is finding a suitable marker. Through determination of the integral intensity of the markers, it is possible to normalize the absorption spectrum of the samples in the series as a result of which the different sample signals are quantitatively comparable. This procedure does not lead to determination of the absolute number of electron spins of a sample in the series.

It is the object of the present invention to present a simplified method for the absolute determination of the number of electron spins in a sample, in particular, wherein it is not necessary to simultaneously measure a similar reference sample for each sample being measured.

SUMMARY OF THE INVENTION

This purpose is achieved by a method of the above-mentioned kind with the following steps:
a) determination of a spatial sensitivity profile f of the RF resonator over the measurement volume;
b) determination of a resonator sensitivity constant c using a calibration sample, which is small, compared to the measurement volume and which has a known number of electron spins at a defined position in the measurement volume,
c) measuring the magnetic resonance signal RS of the extended sample in the apparatus with known spatial distribution of the extended sample within the measuring volume;
d) weighing the magnet resonance signal RS with the integral of the spatial sensitivity profile f of the RF resonator over the partial volume of the measurement volume occupied by the extended sample;
e) determining the number of electron spins $N_S$ in the extended sample as a ratio between the weighted resonance signal as a ratio between the weighted signal and the resonator sensitivity constant c.

In accordance with the current invention, knowledge concerning the properties of the RF resonator, namely the sensitivity profile f and the sensitivity constant c, are evaluated together with the knowledge concerning the spatial distribution of the unknown sample in order to determine the absolute number of electron spins in that sample.

The (substantially constant) properties of the RF resonator can thereby be predetermined and then utilized in the future for all kinds of the samples being measured. A calibrating sample with a known number of electron spins is only required for the measurement of the sensitivity constant c. The spatial distribution of a sample to be measured in a measuring volume of the RF resonator (at a known measurement position of the sample vessel within the measuring volume) can be easily determined from the geometry of the sample holder being used and the degree of filling of that sample vessel. For simplification, a few types of sample vessels can be previously examined having a predetermined equal degree of filling and the associated sample distribution can be stored.

In the simplest case, regular distribution of the substance to be measured can be assumed within the sample vessel (homogenous sample). The spatial distribution (three dimensional) sensitivity profile of the RF resonator leads to determination, for every position in the sample of the extent to which the substance located therein contributes to the ESR absorption spectrum. Generally, the region of the RF resonator closer to the center has a higher sensitivity than in the edge region so that substances disposed in the center of the RF resonator have a stronger contribution to the absorption spectrum than substances disposed near the edge. By means of the summing up (integration) of all contributions of all locations in the sample by means of the sensitivity profile weighting leads to the measured absorption spectrum. Using the sensitivity constant, the integral amplitude of the absorption line can be utilized to determine the absolute number of spins within the absorption spectrum.

Clearly, the method steps in accordance with the invention, in particular the storage of data and the carrying out of calculations for example in method steps d) and e) can be computer based. Clearly, steps a), b) and c) in accordance with the invention can be carried out in arbitrary sequence. However, generally speaking, the steps a) and b) are carried out (and only once) prior to step c).

In accordance with the invention it is, in particular, not necessary to measure a similar or equivalent sample (with the same sample vessel, the same degree of filling of the sample vessel, the same ESR properties etc.) in order to determine the absolute number of spins in a sample. This simplifies and accelerates the absolute electron spin determination to a significant degree.

In particular preferred variation of the method in accordance with the invention, the ESR measurement is a CW-ESR measurement. CW (continuous wave) ESR measurements are properly suited for the method in accordance with the invention, since the absorption spectra or its derivative directly contains the measurement result. The integral over the absorption line (or the double integral over the differentially determined absorption lines) is directly proportional to the number of electron spins (i.e. with homogenous samples to the concentration of the ESR active substance within the sample).

In a further development of this variation which is particular advantageous, the weighting in step d) is determined in accordance with the following formula:

$$DI = c \cdot \sqrt{P} \cdot B_m \cdot Q \cdot V \cdot C \cdot S(S+1) \cdot n_B \cdot f(B_1, B_m)$$

wherein
c=the resonator sensitivity constant
P=the microwave power/MW
$B_m$=the modulation amplitude/G
Q=the Q-factor of the resonator
V=a sample volume/L
C=the sample concentration/M
S=the electron spin
$n_B$=the Boltzman factor for the temperature dependence
$f(B_1, B_m)$=the spatial sensitivity distribution of the RF resonator
$B_1$=the RF field amplitude
DI=the double integral of the differentially taken ESR absorption line (DE corresponds to RS).

Use of this formula permits weighting in accordance with the invention using homogenous samples.

In a preferred method variation, step a) is effected by means of imaging ESR. In this manner, the resonator sensitivity profile f can be easily determined. The imaging ESR measurement is mostly simply carried out using a sample, which is homogenous throughout the entire measurement volume.

In an advantageous method variation, the defined position within the measurement volume in the vicinity of the higher sensitivity of the RF resonator is chosen in step b). In this fashion, a particularly good signal to noise relationship can be achieved; the determination of the sensitivity constant is then particularly precise. In general, the region of higher sensitivity is in the center of the RF resonator. Therefore, the defined position in accordance with the invention is also preferentially in the center of the RF resonator. Clearly, the size of the calibration sample in the position of the defined position should be chosen in such a fashion that no substantial change in the sensitivity profile occurs over the volume of the calibration sample.

In a particularly preferred variation of the method in accordance with the invention, the sensitivity profile f of the RF resonator is approximated as being constant in two spatial directions, wherein the longest extent of the extended sample in the measurement volume is in a third spatial direction, whereby the three spatial directions are mutually orthogonal. This variation leads to substantial simplification of the method steps a) and d) and thereby renders the procedure more rapid. In the event that the extent of the sample (the partial volume) is small in the first and second spatial directions compared to the size of the measurement volume and if the partial volumes are disposed in the center of the resonator, the above approximation normally leads to substantially precise results. Samples in vials are particularly suitable for this variation.

In a preferred further development of this method variation, the partial volume is cylinder shaped and the cylinder axis of the partial volume is in the third spatial direction. The above-mentioned approximation leads to very precise results within a cylindrically symmetric partial volume directed in this manner.

In a preferred variation of the method in accordance with the invention, the sample is disposed in a vial and the spatial distribution of the extended measuring samples is determined by means of the filled height in the vial and the position of the vial within the measurement volume, in particular, a lower end of the vial. Vials have been shown to be suitable as sample holders for ESR. The filing height of the vial is easy to determine, in particular optically and even with the naked eye, with a scale or with a calibration line. The position of a sample vial within the measuring volume can generally not be changed at all or only in the third spatial direction (for adjustment to a particular vial length) whereby the lower seating of the sample vial is simplest to adjust. The position of the seating (and thereby of the vial) can therefore also be determined by simple means such as a laser distance measurement or using a scale or an adjustable screw.

Further advantages of the invention can be extracted from the description and the drawings, the above-mentioned features and those to be mentioned below can be utilized in accordance with the invention individually or collectively in arbitrary combination. The examples shown and described are not to be considered exhaustive enumerations rather have exemplary character for illustrating the invention.

The invention is shown in the drawing and is more closely explained with regard to embodiments.

DESCRIPTION OF THE PREFERRED EMBODIMENT

Figure 1A:
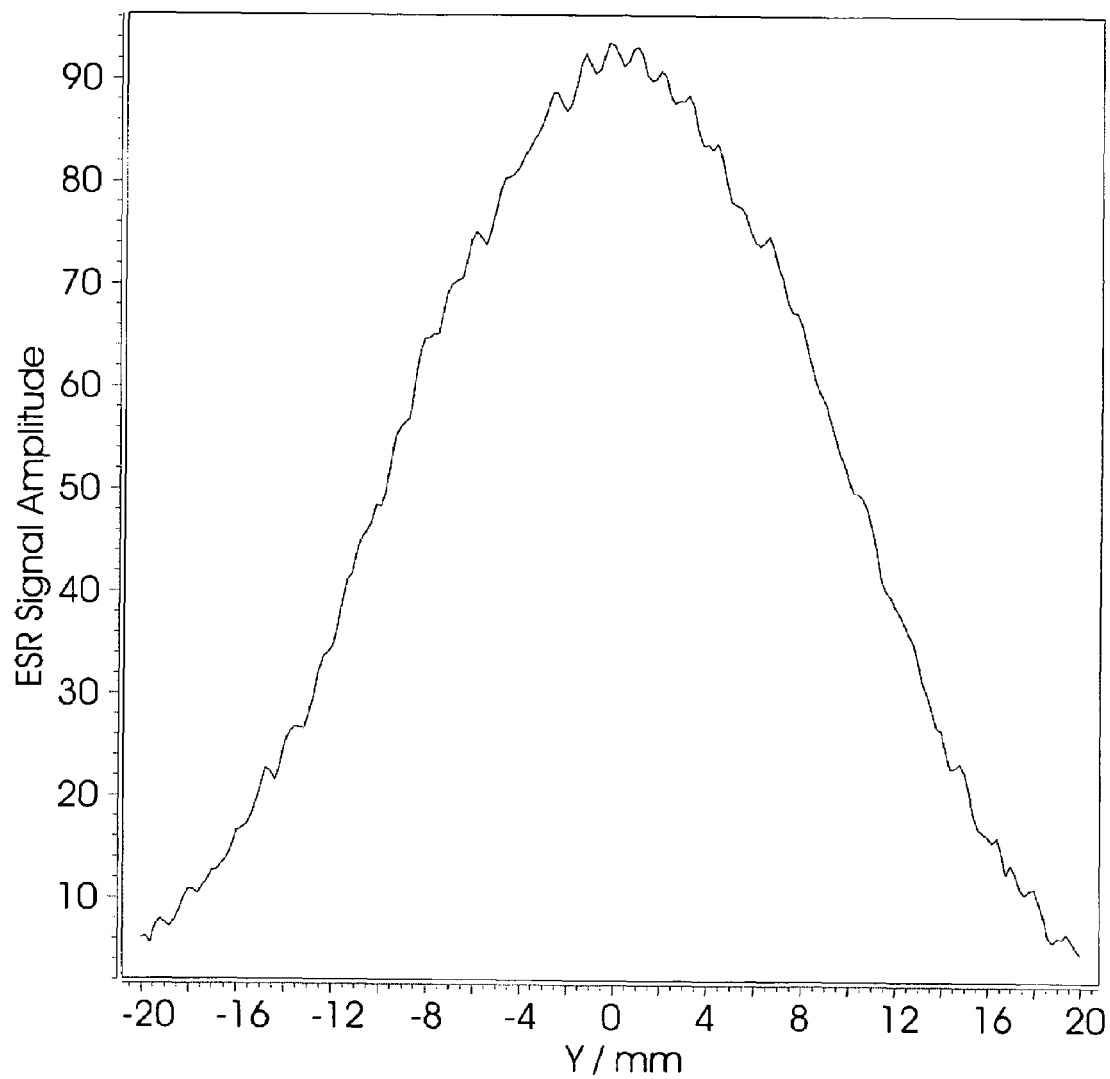
FIGS. 1a through 1c show the sensitivity profile of a cylindrical ESR resonator for utilization within the context of the method in accordance with the invention.

The invention describes a new method of absolute quantification of electron spins in samples using ESR. The method is particularly suitable for the measurement of a plurality of differing samples, in particular in differing sample vessels without having to carry out a reference measurement for each sample type.

Below is described, by way of example, the individual steps in accordance with the invention for determining the absolute number of electron spins of a paramagnetic sample. The sample measurement is thereby carried out in an ESR apparatus having a RF resonator.

1. Measurement of the Calibration Sample for Determining the Sensitivity Constant c.

A point sample with a known number of spins is used to determine the resonator calibration factor (c) at one point within the resonator. In a practical embodiment, the sample point is chosen to be the center of the resonator where this resonator has the highest sensitivity. The spatial distribution of the sample point must be substantially smaller than the sensitive volume (measurement volume) of the resonator. With this measurement, all instrumental parameters, which contribute to the signal amplitude, are registered (P, Q, $B_m$, number of spins, temperature, see equation 1 for the EPR signal):

$$DI = c \cdot \sqrt{P} \cdot B_m \cdot Q \cdot V \cdot C \cdot S(S+1) \cdot n_B \cdot f(B_1, B_m) \quad \text{(equation 1)}$$

c=the calibration factor
P=the microwave power/mW
$B_m$=the modulation amplitude/G
Q=the q-factor of the resonator
V=a sample volume/L
C=the sample concentration/M
S=the electron spin
$n_B$=the Boltzman factor for the temperature dependence
$f(B_1, B_m)$=the spatial sensitivity distribution of the RF resonator wherein the dependence between the Boltzman factor and the sample temperature is:

$$n_B = \frac{1 - e^{\frac{-h \cdot v}{k_b \cdot T}}}{1 + e^{\frac{-h \cdot v}{k_b \cdot T}}} \quad \text{(equation 4)}$$

v=the microwave frequency/Hz
T=the sample temperature/K

As a result of this measurement, the double integral (DI) of the differentially measured absorption line is noted, which, in turn is proportional to the number of spins (equation 1). The calibration factor (c) can then be calculated (equation 2 for determination of c using the calibration sample):

$$c = \frac{DI}{\sqrt{P} \cdot B_m \cdot Q \cdot V \cdot C \cdot S(S+1) \cdot n_B \cdot f(B_1, B_m)} \quad \text{(equation 2)}$$

$$= \frac{DI}{\sqrt{P} \cdot B_m \cdot Q \cdot N_S \cdot S(S+1) \cdot n_B \cdot f(B_1, B_m)}$$

$N_S$=the number of spins in the resonator during the calibration.

One should note that no particular requirements must be made with regard to the calibration sample other than the fact that it has sufficient precision with respect to the number of spins.

2) Unknown Point Sample

The number of spins of any arbitrary point sample (at the same location) can then be determined by the calculated double integral (equation 5). For a point sample $f(B_1, B_m) = 1$.

$$N_S = \frac{DI}{c \cdot \sqrt{P} \cdot M \cdot Q \cdot S(S+1) \cdot n_B \cdot f(B_1, B_m)} \quad \text{(equation 5)}$$

$N_S$=the number of spins

However, generally speaking, an unknown sample is extended so that the resonator properties must be considered.

3) Sensitivity Profile f of the Resonator

Due to the electromagnetic properties of the resonator, the sensitivity is position sensitive and is described by the function f(x) with x being a (generally vector) positioned variable. With known position dependencies this can, for its part, be used as a correction for the double integral.

4) Determination of a Sensitivity Profile f

The position dependence of the resonator sensitivity can be measured using ESR imaging experiments. Towards this end, the signal amplitude of a homogenous sample (solution) is measured in space using the maximum possible volume (which is a resonator property in the X band the sample vials can have a diameter of up to 10 mm).

These data are used to determine a correction function $f(B_1, B_m)$ (the electromagnetic quantities $B_1$ and $B_m$ are responsible for the position dependence). Equation 3 gives the definition of $f(B_1, B_m)$:

$$f(B_1, B_m) = \frac{\int_a^b f(x) \, dx}{\int_a^b F(x) \, dx} \quad \text{(equation 3)}$$

a=the beginning of the sample position
b=the end of the sample position
F(x)=a rectangular function for the resonance shape (ideal case)
f(x)=the measured resonator shape.

Remarks: f(x) is, by way of example, determined by a polynomial fit of tenth order from the measured profile.

Figure 1B:
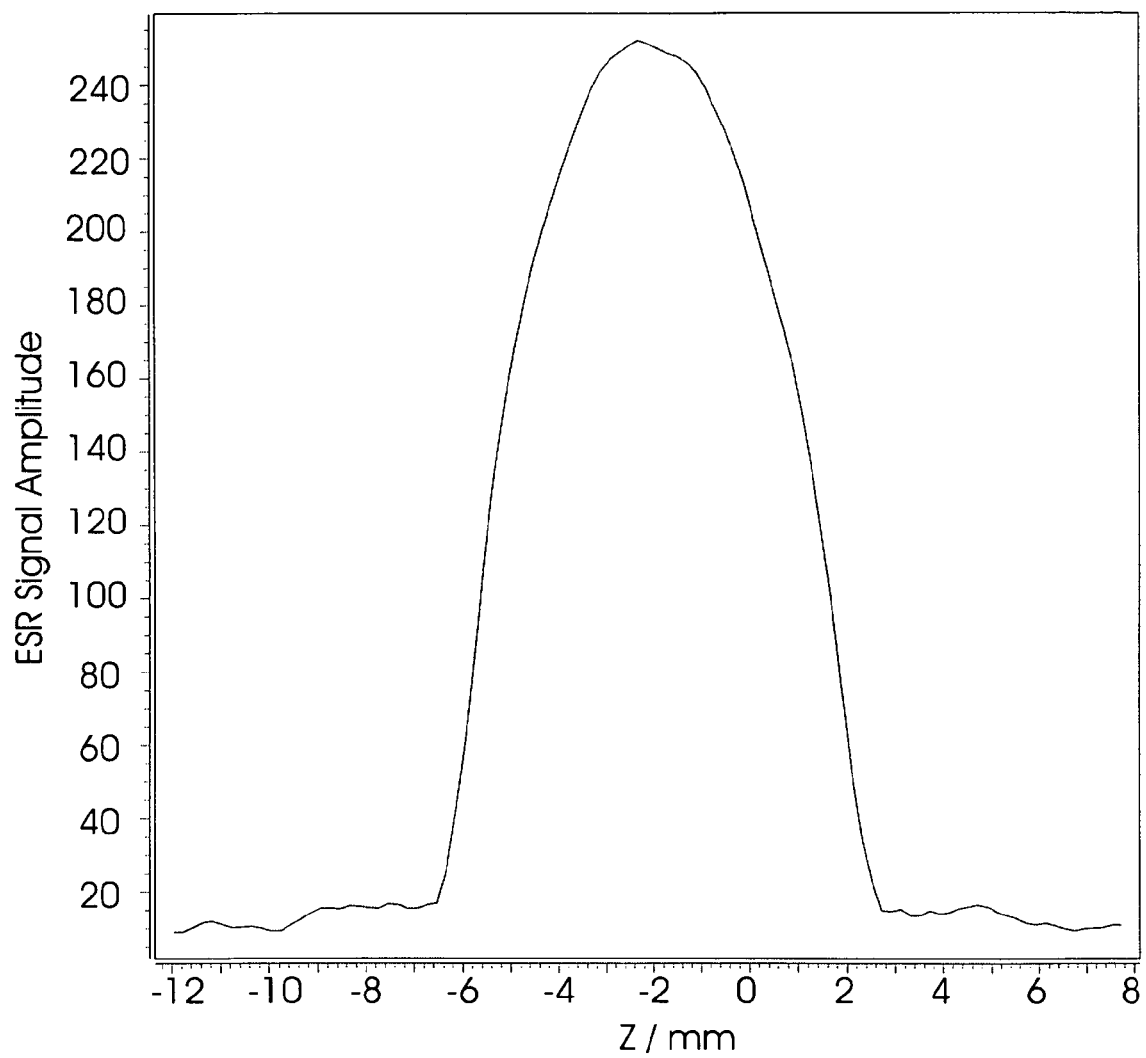
Figure 1C:
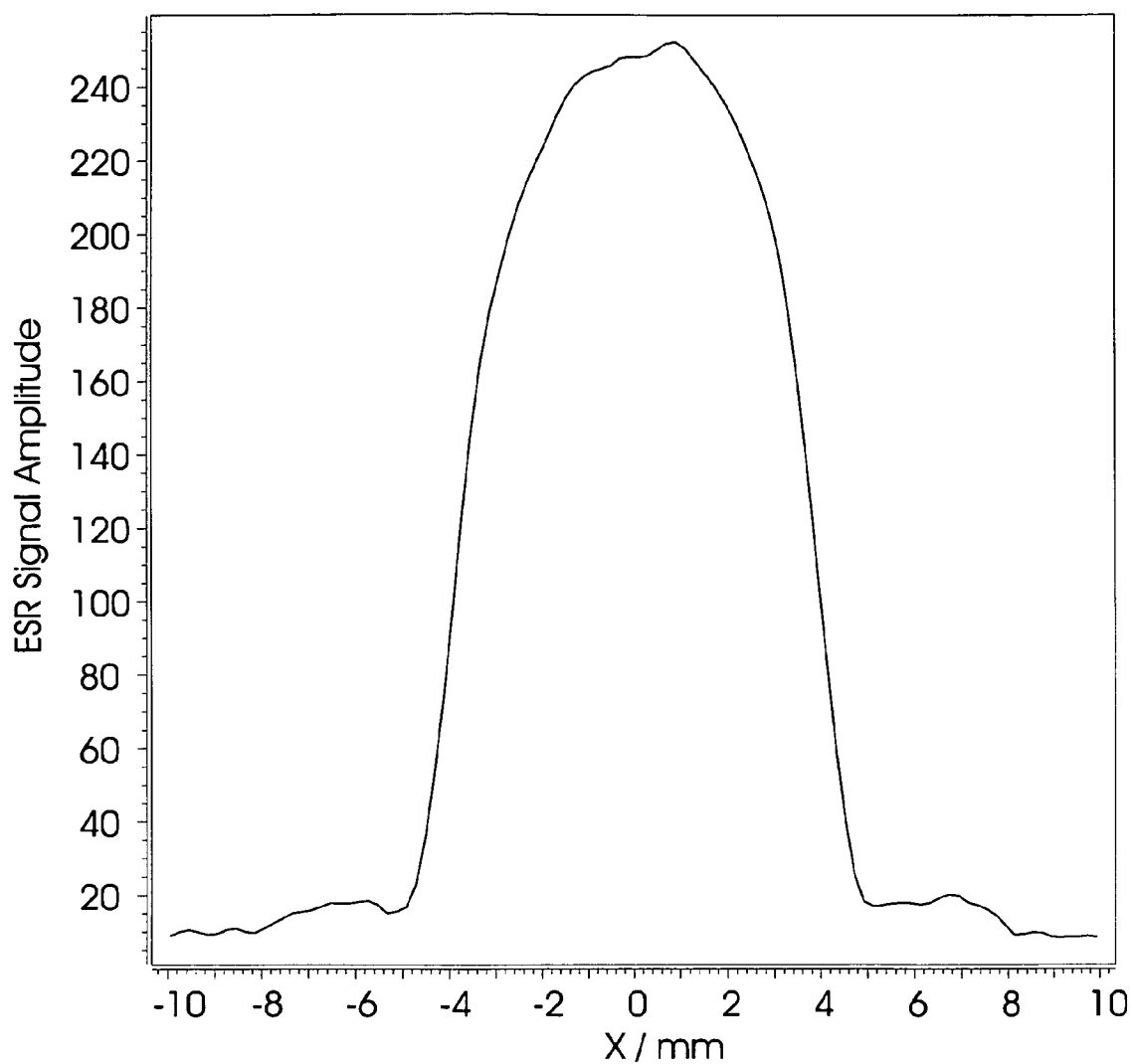

FIGS. 1a through 1c show, by way of example, measured shapes for the sensitivity of an ESR resonator (cylindrical resonator of type Bruker ER422SHQE) in three orthogonal spatial directions Z (FIGS. 1a, c, FIG. 1b) and X (FIG. 1c). In each case, the position coordinate in the spatial direction is shown in millimeters and plotted against the ESR signal in the homogenous imaging sample. The Y axis corresponds to the axis of the sample vial. Typical sample vials have an inner diameter of less than or equal to 4 mm.

The choice of the imaging sample is not subject to any limitations aside from the fact that it must be homogenous and suitable for the imaging experiment (that requires a significantly narrow line compared to the available gradient strength).

5) Number of Spins in the Extended Unknown Sample

The number of spins of an unknown sample, which is located when the volume measured in the previous step 4, can be determined using equation 5;

$$N_S = \frac{DI}{c \cdot \sqrt{P} \cdot M \cdot Q \cdot S(S+1) \cdot n_B \cdot f(B_1, B_m)} \quad \text{(equation 5)}$$

$N_S$=the number of spins

The instrumental parameters B, $B_{mod}$, Q, and T are usually registered for each measurement. The spatial extent of the unknown sample is used in order to determine the correction function $f(B_1, B_m)$.

6) Differing Types of Samples

A reference sample is no longer necessary for all of the following types of measurements and differing sample types. The resonator properties (c and f(x)) can be determined once for each type of resonator (e.g. rectangular resonator, cylindrical resonator) using the ESR imaging experiment. Each resonator is therefore suitable for these methods of quantification.

7) Approximation for Thin Samples

For some types of resonators, the sensitivity in the Z, X plane is sufficiently constant so that correction over the sensitivity profile in first approximation must only be carried out in the Y-direction (sample axis).

For the profile in FIGS. 1b and 1c, by way of example, one can assume the sensitively profile in the X and Z directions to be constant (i.e. maximum correspondence with the measured profile) without significant loss of accuracy if the sample has an inner diameter of 1 mm (which corresponds to the extent in the Z and X directions) and by placing the sample vial at the maximum of the sensitivity.

Figure 2:
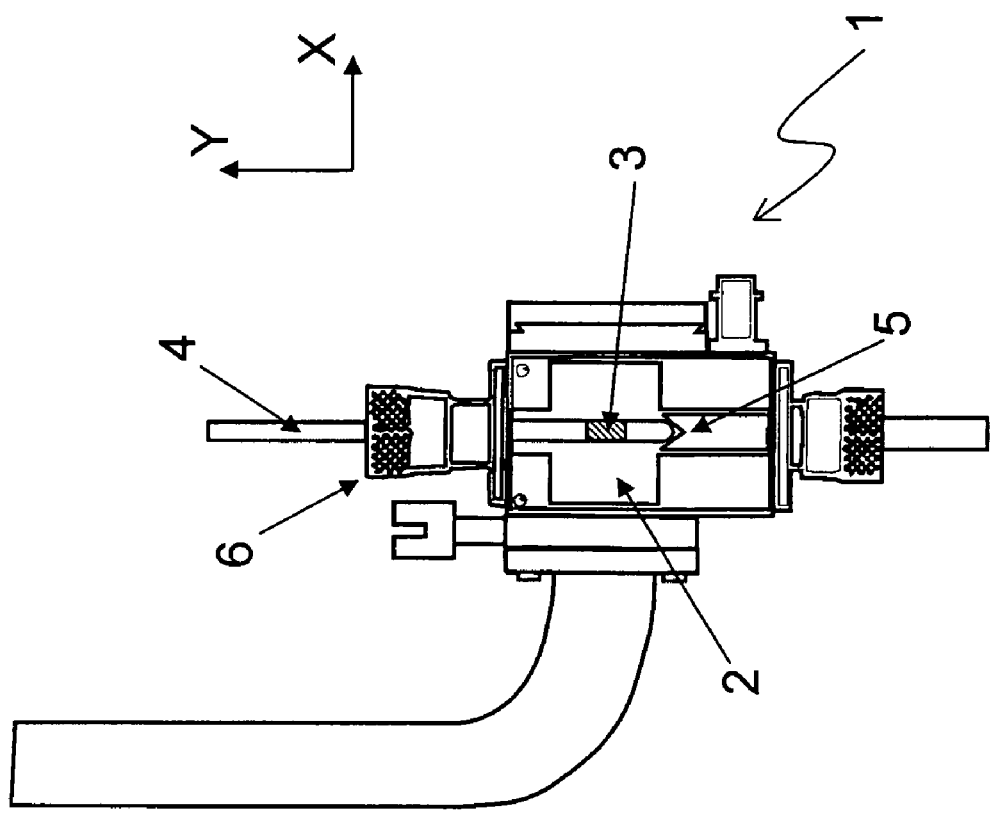
FIG. 2 shows a schematic cross-section through an ESR resonator for carrying out the method in accordance with the invention.

FIG. 2 schematically shows an ESR resonator 1 for carrying out the method in accordance with the invention. The resonator 1 defines a measurement volume (resonator volume) 2 in which sample 3 is disposed. The sample 3 has three-dimensional extent and occupies a portion of the measurement volume 2. The portion of the measurement volume 2 occupied by the sample 3 is also designated as the partial volume. In the example shown the sample 3 is configured as a sample plug within a sample vial 4. That partial volume has a cylindrical shape.

The low end of the sample vial 4 is held in a centered abutment 5. The position of the sample 3 and of the partial volume within the resonator can be determined from the position of the lower and the upper meniscus of the sample relative to the lower end of the sample volume 4 in a straight forward fashion in conjunction with an associated further centering of the sample vial 4 using an upper clamp 6 on the resonator 4.

Within the context of the invention, the sensitivity profile f of the resonator 1 is determined within the measurement volume 2. Towards this end, it is sufficient to measure the resonator volume to such and extent as is necessary for the largest sample being used.

We claim:

1. A method for determination of the absolute number of electron spins in an extended sample with the assistance of an apparatus for measuring magnetic resonance, the extended sample being disposed within a measurement volume of a radio frequency (RF) resonator of the apparatus during an electron spin resonance measurement, the method comprising the steps of:
   a) determining a spatial sensitivity profile of the RF resonator over the measurement volume;
   b) determining, at a defined position within the measurement volume, a resonator sensitivity constant using a calibration sample which is small compared to the measurement volume, the calibration sample having a known number of electron spins;
   c) measuring a magnetic resonance signal of the extended sample in the apparatus, wherein the extended sample has a known spatial distribution in the measurement volume;
   d) weighting the magnetic resonance signal with an integral of the spatial sensitivity profile of the RF resonator over a partial volume of the measurement volume occupied by the extended sample; and
   e) determining a number of electron spins in the extended sample as a quotient between a weighted resonance signal of step d) and the resonator sensitivity constant of step b).

2. The method of claim 1, wherein the ESR measurement is carried out as a cw ESR measurement.

3. The method of claim 2, wherein the weighting in step d) is carried out in accordance with the following formula:

$$DI = c \cdot \sqrt{P} \cdot B_m \cdot Q \cdot V \cdot C \cdot S(S+1) \cdot n_B \cdot f(B_1, B_m)$$

with
   c=the resonator sensitivity constant
   p=microwave power/mW
   $B_m$=the modulation amplitude/G
   Q=the quality factor of the resonator
   V=a sample volume/L
   C=the sample concentration/M
   S=the electron spin
   $n_B$=Boltzman factor for the temperature dependence
   $f(B_1, B_m)$=the spatial sensitivity distribution of the RF resonator
   $B_1$=the RF field amplitude
   DI=the double integral of the differential measured ESR absorption line.

4. The method of claim 1, wherein step a) is effected using imaging ESR.

5. The method of claim 1, wherein, in step b), the defined position in the measuring volume is chosen within a region of higher sensitivity of the RF resonator.

6. The method of claim 1, wherein the spatial sensitivity profile of the RF resonator is approximated as being constant in two spatial directions (X, Z), wherein a third spatial direction (Y) lies along a longest extension of the extended sample within the measuring volume, wherein the three spatial directions (X, Y, Z) are mutually orthogonal.

7. The method of claim 6, wherein the partial volume is cylindrical in shape and a cylindrical axis of the partial volume lies in the third spatial direction (Y).

8. The method of claim 7, wherein the sample is disposed in a vial and a spatial distribution of the extended sample is determined by means of a fill height within the vial and a position of the vial within the measuring volume or a position of a lower vial end thereof.

* * * * *